United States Patent
Shen et al.

(10) Patent No.: US 11,434,226 B2
(45) Date of Patent: Sep. 6, 2022

(54) SALT AND POLYMORPH OF BENZOPYRIMIDINONE COMPOUND AND PHARMACEUTICAL COMPOSITION AND USE THEREOF

(71) Applicants: SHANGHAI INSTITUTE OF MATERIA MEDICA, CHINESE ACADEMY OF SCIENCES, Shanghai (CN); SUZHOU VIGONVITA LIFE SCIENCES CO., LTD., Jiangsu (CN); TOPHARMAN SHANGHAI CO., LTD., Shanghai (CN)

(72) Inventors: Jingshan Shen, Shanghai (CN); Yang He, Shanghai (CN); Weiming Chen, Shanghai (CN); Jianfeng Li, Shanghai (CN); Guanghui Tian, Jiangsu (CN); Xudong Gong, Shanghai (CN); Zhen Wang, Shanghai (CN); Rongxia Zhang, Shanghai (CN); Yongjian Liu, Shanghai (CN); Hualiang Jiang, Shanghai (CN)

(73) Assignees: SHANGHAI INSTITUTE OF MATERIA MEDICA, CHINESE ACADEMY OF SCIENCES, Shanghai (CN); SUZHOU VIGONVITA LIFE SCIENCES CO., LTD., Jiangsu (CN); TOPHARMAN SHANGHAI CO., LTD., Shanghai (CN)

( * ) Notice: Subject to any disclaimer, the term of this patent is extended or adjusted under 35 U.S.C. 154(b) by 87 days.

(21) Appl. No.: 16/736,300

(22) Filed: Jan. 7, 2020

(65) Prior Publication Data

US 2020/0140415 A1    May 7, 2020

Related U.S. Application Data

(63) Continuation of application No. PCT/CN2018/093965, filed on Jul. 2, 2018.

(30) Foreign Application Priority Data

Jul. 7, 2017   (CN) .......................... 201710551480.4

(51) Int. Cl.
 *C07D 403/12* (2006.01)
 *A61K 45/06* (2006.01)

(52) U.S. Cl.
 CPC ............ *C07D 403/12* (2013.01); *A61K 45/06* (2013.01); *C07B 2200/13* (2013.01)

(58) Field of Classification Search
 CPC .......................... C07D 403/12; C07B 2200/13
 See application file for complete search history.

(56) References Cited

FOREIGN PATENT DOCUMENTS

| CN | 1746171 A | 3/2006 |
|---|---|---|
| EP | 0 636 626 A1 | 2/1995 |
| WO | WO 2009/106531 A1 | 9/2009 |
| WO | 2010/066111 A1 | 6/2010 |

OTHER PUBLICATIONS

Berge et al. J. Pharm. Sci., 1977, 66 (1), 1-19.*

* cited by examiner

*Primary Examiner* — Alicia L Otton
(74) *Attorney, Agent, or Firm* — Reinhart Boerner Van Deuren P.C.

(57) ABSTRACT

The present disclosure relates to a salt of phenyl pyrimidinone compound, a polymorph thereof and a pharmaceutical composition comprising the same and a use thereof, particularly relates to the hydrochlorate of phenyl pyrimidinone compound of following formula (I-A) and a pharmaceutically acceptable polymorph, solvate, hydrate, co-crystal, anhydrous substance, or amorphous form thereof, a pharmaceutical composition and a pharmaceutical unit dosage comprising the same, the preparing method and use thereof.

4 Claims, 6 Drawing Sheets

SALT AND POLYMORPH OF BENZOPYRIMIDINONE COMPOUND AND PHARMACEUTICAL COMPOSITION AND USE THEREOF

CROSS-REFERENCE TO RELATED PATENT APPLICATIONS

This patent application is continuation of PCT Application No. PCT/CN2018/093965, filed Jul. 2, 2018, which claims priority to Chinese Application No. 201710551480.4, filed Jul. 7, 2017, the entire teachings and disclosure of which are incorporated herein by reference thereto.

TECHNICAL FIELD

The present invention relates to a salt of 5,6-diethyl-2-[2-n-propoxy-5-(2-(4-methylpiperazin-1-yl)acetamido)phenyl]pyrimidin-4(3H)-one (compound Z) and a polymorph thereof, as well as a pharmaceutical composition containing the same, to a method for preparing the salt and the polymorph, and a use thereof in the preparation of the pharmaceutical composition.

BACKGROUND OF THE INVENTION

A series of compounds having PDE5-inhibiting activity are disclosed in the international published application No. WO2010/066111 and the compounds exhibit extremely high activity and selectivity for PDE5 enzyme in the in vitro screening tests as enzyme inhibitors. Compound 5,6-diethyl-2-[2-n-propoxy-5-(2-(4-methylpiperazin-1-yl)acetamido)phenyl]pyrimidin-4(3H)-one (compound Z) is included therein, which is represented by the following structural formula:

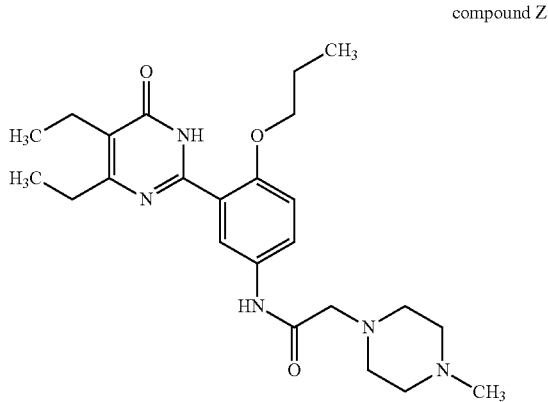 [SMILES: CCCOc1ccc(NC(=O)CN2CCN(C)CC2)cc1-c1nc(CC)c(CC)c(=O)[nH]1]

compound Z

SUMMARY OF THE INVENTION

The inventors of the present application found that compound Z in a free state has poor solubility in water and thus is, hard to be solved, which will have a negative influence on the process of a pharmaceutical formulation preparation; on the other hand, the compound itself has a pungent odor, which will result in a negative influence when applied as a pharmaceutical preparation for human. It is therefore an object of the present invention to develop a suitable form of compound Z for the preparation of a drug, which should have the advantages of good stability, high water solubility, low hygroscopicity, no bad odor and the like.

The physical properties of the pharmaceutical compounds and their salts, as well as the crystalline and amorphous substance thereof have a great impact on the bioavailability of the drug, the purity of the active pharmaceutical ingredient, and the formulation of the preparation. Therefore, during the drug development, it is necessary to study what kind of salt, crystal form, and amorphous form of the compound are preferred. Since the above physical properties depend on the properties of various compounds, it is usually difficult to predict the original medicinal salts, crystal forms, and amorphous substances having good physical properties, and thus various studies should be required for each compound.

Accordingly, it is another object of the present invention to provide various salts of compound Z and their crystals and amorphous forms thereof, which have the advantages of high stability, low hygroscopicity, high purity, and ease of drug processing and formulation.

The present inventors synthesized and separated various salts of compound Z and crystallization forms thereof, and studied various physical and chemical properties thereof, and found the salts of compound Z and crystallization forms and solvated forms thereof having good physical properties, which can be used as an active pharmaceutical ingredient or as an intermediate for the preparation of the active pharmaceutical ingredient, so as to accomplish the present invention.

The present invention relates to a salt of compound 5,6-diethyl-2-[2-n-propoxy-5-(2-(4-methylpiperazin-1-yl)acetamido)phenyl]pyrimidin-4 (3H)-one (compound Z) and a polymorph thereof, and a pharmaceutical composition and a pharmaceutical unit dosage form containing the same. The invention further relates to a co-crystal or complex of compound Z, as well as a pharmaceutical composition comprising the same. The invention also relates to a process for the preparation of the above substances.

In one aspect of the invention, it provides a compound represented by formula (I) and a pharmaceutically acceptable polymorph, solvate, hydrate, co-crystal, anhydrous or amorphous form thereof:

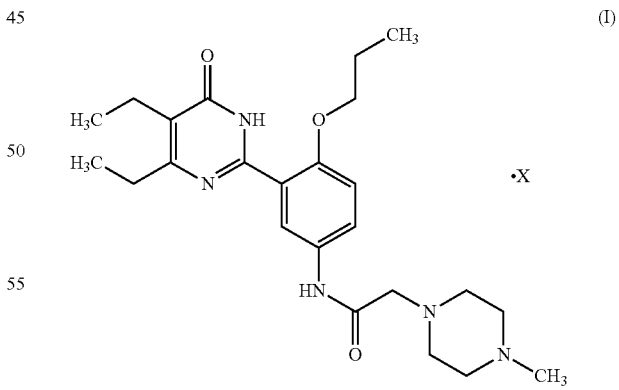

(I)

wherein X includes, but is not limited to, an organic acid or an inorganic acid. For example, the organic acid may include, but is not limited to, maleic acid, succinic acid, citric acid, tartaric acid, fumaric acid, formic acid, acetic acid, propionic acid, malonic acid, oxalic acid, benzoic acid, phthalic acid, methanesulfonic acid, benzenesulfonic acid, toluenesulfonic acid, naphthalenesulfonic acid, 1,5-naphthalenedisulfonic acid, camphoric acid, camphorsulfonic acid, salicylic acid, acetylsalicylic acid, aspartic acid, glutamic acid, lactic acid, glucose acid, ascorbic acid, gallic acid, mandelic acid, malic acid, sorbic acid, trifluoroacetic acid, taurine, homotaurine, 2-hydroxyethanesulfonic acid, cinnamic acid, mucic acid; and the inorganic acid may include, but is not limited to, hydrochloric acid, hydrobromic acid, hydroiodic acid, sulfuric acid, nitric acid, phosphoric acid, perchloric acid; and other similar protic acids.

wherein, X is preferably maleic acid, succinic acid, citric acid, tartaric acid, fumaric acid, mucic acid, acetic acid, methanesulfonic acid, hydrochloric acid, nitric acid or sulfuric acid.

X is more preferably hydrochloric acid, i.e. the compound of formula (I) is preferably a compound of formula (I-A):

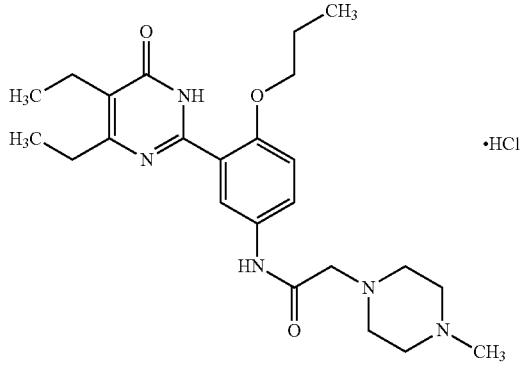

(I-A)

More preferably, the compound of formula (I) is a crystalline form A or B of the hydrochlorate of compound Z. For the crystalline form A, diffraction peaks are observed at a diffraction angle 2θ of 9.3°±0.2°, 12.2°±0.2°, 16.7°±0.2° in X-ray diffraction pattern, more specifically, at a diffraction angle 2θ of 6.1°±0.2°, 9.3°±0.2°, 11.1°±0.2°, 12.2°±0.2°, 15.3°±0.2°, 16.7°±0.2°, 21.6°±0.2°, 22.9°±0.2° in X-ray diffraction pattern. The crystalline form A is a monohydrate having the following structure:

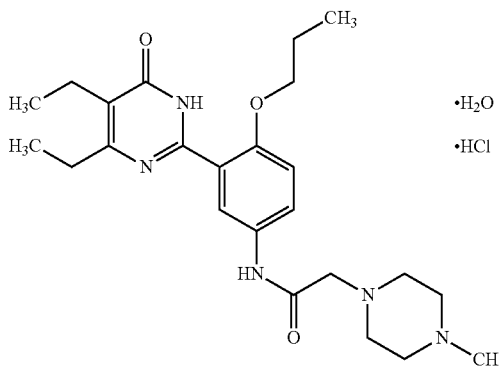

For the crystalline form B, diffraction peaks are observed at a diffraction angle 2θ of 12.5°±0.2°, 13.5°±0.2°, 17.9°±0.2°, 19.5°±0.2°, 19.9°±0.2°, 23.0°±0.2°, 26.5°±0.2°, 26.8°±0.2° in X-ray diffraction pattern, more specifically, at a diffraction angle 2θ of 12.5°±0.2°, 12.8°±0.2°, 13.5°±0.2°, 14.1°±0.2°, 17.9°±0.2°, 19.5°±0.2°, 19.9°±0.2°, 23.0°±0.2°, 26.5°±0.2°, 26.8°±0.2° in X-ray diffraction pattern. The crystalline form A of the hydrochlorate of compound Z is most preferable.

The present invention further provides a single-crystal of crystalline form A of the hydrochlorate of compound Z. The single crystal of form A is studied by the single crystal X-ray diffraction analysis, the single crystal X-ray diffraction pattern is shown in FIG. 9, which shows: crystal system: monoclinic, space group: Pc, axis length: a=9.935(4) Å, b=14.44(6) Å, c=9.147(5) Å, the angle of the lattice plane: α=90°, β=106.47(5°), γ=90°, volume=1260.5(11) Å$^3$, and the number of molecules per unit cell is Z=2.

The single crystal structure is measured by an X-ray single crystal diffractometer, the manufacturer: Japanese Science (Japan Corporation (rigaku)); instrument model: SuperNova, Dual, Cu at zero, AtlasS2; Detection temperature: 100K.

The crystalline form A of the present invention comprises an amount of 3.28 to 5.35 wt % of water, and more specifically an amount of 3.28 to 3.98 wt % of water. The amount of water is determined by the Karl Fischer method.

As used herein, the term "salt" or "salts" includes a pharmaceutically acceptable salt, as well as a pharmaceutically unacceptable salt. It is not preferable to apply a pharmaceutically unacceptable salt to the patient, but the salt can be used to provide pharmaceutical intermediates and bulk pharmaceutical forms.

As used herein, the term "pharmaceutically acceptable salt" or "pharmaceutically acceptable acid addition salt" refers to a salt prepared by using a pharmaceutically acceptable acid and compound Z, including, but not limited to, an organic acid salt and an inorganic acid salt, preferably the salt of maleic acid, succinic acid, citric acid, tartaric acid, fumaric acid, mucic acid, acetic acid, methanesulfonic acid, hydrochloric acid, nitric acid or sulfuric acid, most preferably the salt of methanesulfonic acid, fumaric acid or hydrochloric acid.

Another embodiment of the invention relates to a pharmaceutical composition and dosage form comprising a therapeutically or prophylactically effective amount of compound of formula (I), or a polymorph, solvate, hydrate, co-crystal, anhydrous substance, or amorphous substance thereof.

Optionally, by placing the salt of the compound of formula (I) of the present invention in air or by recrystallization, a hydrate with adsorbed water will be formed by absorbing water, and acid addition salts containing such kind of adsorbed water are also included in the present invention.

The term "solvate" of the present invention is not particularly limited as long as it is formed by a solvent used for the production or crystalline of a salt, and specifically, for example, it may be a hydrate, an alcohol solvate, an acetone solvate, a toluene solvate. The hydrate and alcohol solvate are preferable.

A further embodiment of the invention relates to a process for the preparation of a pharmaceutical composition and dosage form comprising a compound of formula (I), or a polymorph, solvate, hydrate, co-crystals anhydrate, or amorphous form thereof.

The specific preparation method is as follows.

1. Method for Preparing the Salt of 5,6-diethyl-2-[2-n-propoxy-5-(2-(4-methylpiperazin-1-yl)acetamido)phenyl]pyrimidin-4(3H))-one (Compound of Formula I)

Compound Z can be prepared by reference to the example of WO2010/066111. Compound Z can also be prepared by the following method:

1) Subjecting compound Z-3 and dimethyl sulfate to a methylation reaction in the presence of a base to obtain compound Z-4;
2) Reacting compound Z-4 with ammonia to obtain compound Z-5;
3) Subjecting compound Z-5 and methyl 2-ethyl-3-oxopentanoate to a dehydration and cyclization reaction in the presence of a base to obtain compound Z,

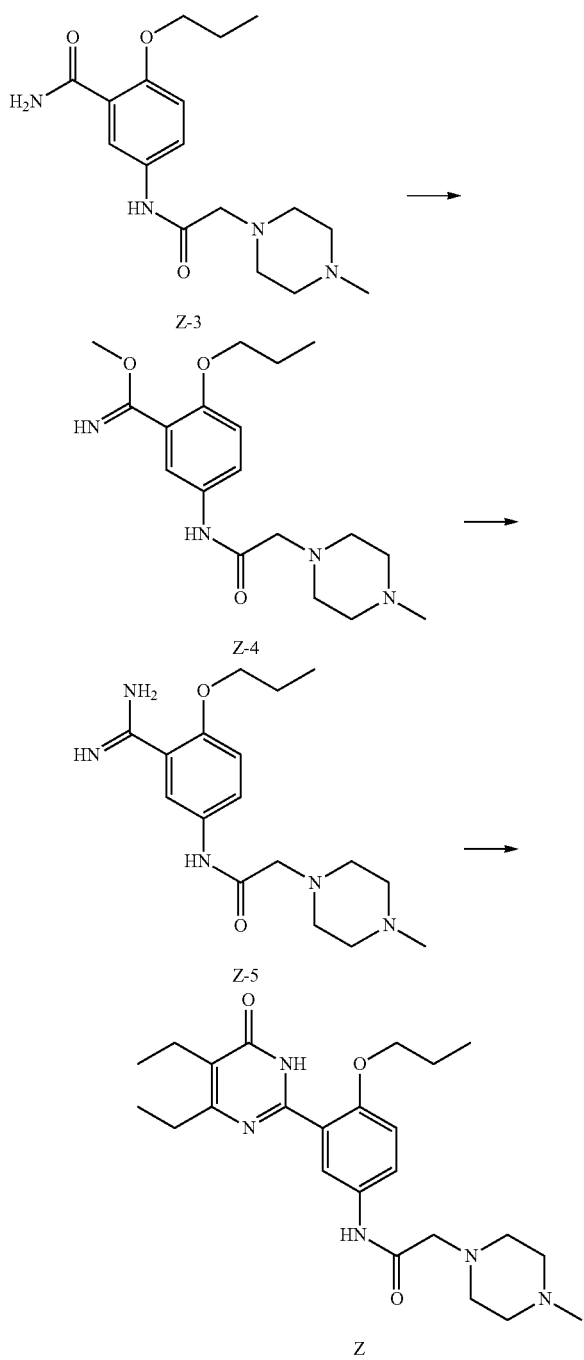

Wherein, in the above step 1), the reaction temperature is usually from room temperature to 100° C., the solvent is preferably dichloromethane, toluene, chloroform or N,N-dimethylformamide, the base is preferably potassium carbonate or sodium carbonate;

In the above step 2), the reaction temperature is usually at 0° C.~50° C., the solvent is preferably methanol, ethanol or N,N-dimethylformamide;

In the above step 3), the reaction temperature is usually at 50–120° C., the solvent, preferably chloroform, methanol, ethanol, ethylene glycol monomethyl ether, N,N-dimethylformamide or 1,4-dioxane. The base is preferably potassium carbonate, sodium carbonate, sodium methoxide or sodium ethoxide.

The compound of the formula (I) can be prepared by forming a salt through a reaction of the corresponding acid with compound Z, for example, by using one of the following methods:

Method I:
1) dissolving compound Z in a first solvent to form solution a;
2) dissolving a corresponding acid X in a second solvent to form solution b;
3) adding solution a to solution b, or adding solution b to solution a to prepare a mixed solution, and separating the salt of compound Z (i.e. the compound of formula I) from the mixed solution;

Method II:
1) dissolving compound Z in a first solvent to form solution a;
2) directly adding a corresponding acid X to solution a, and then separating the salt of compound Z (i.e. the compound of the formula I) from the solution;

Method III:
1) dissolving a corresponding acid X in a second solvent to form solution b;
2) directly adding compound Z to solution b, and then separating the salt of compound Z (i.e. a compound of formula I) from the solution;

Preferably, the compound of the formula (I-A) can be prepared by forming a salt through the reaction of hydrogen chloride with compound Z, for example, by using one of the following methods:

Method I:
1) dissolving compound Z in a first solvent to form solution a;
2) dissolving hydrogen chloride in a second solvent to form solution b;
3) adding solution a to solution b, or adding solution b to solution a, to prepare a mixed solution, and separating the hydrochlorate of compound Z (i.e. the compound of formula (I-A)) from the mixed solution;

Method II:
1) dissolving compound Z in a first solvent to form solution a;
2) directly adding hydrogen chloride to solution a, and separating the hydrochlorate of compound Z (i.e., the compound of formula (I-A)) from the solution;

Method III:
1) dissolving hydrogen chloride in a second solvent to form solution b;
2) directly adding compound Z to solution b, then separating the hydrochlorate of compound Z (i.e. the compound of formula (I-A)) from solution.

In the above method, the first and second solvents are each independently selected from water, a non-aqueous solvent and a mixed solvent thereof, and more particularly, selected from water, alcohols, ethers, esters, hydrocarbons, ketones and mixed solvents thereof and the like. More specifically, the first solvent and the second solvent are each independently one or more selected from water; esters such as ethyl acetate, methyl acetate, propyl acetate, butyl acetate, methyl formate, ethyl formate, propyl formate, butyl formate; alcohols such as methanol, ethanol, propanol, isopropanol, butanol, ethylene glycol, propylene glycol; ethers such as diethyl ether, propyl ether, isopropyl ether, petroleum ether, ethylene glycol monomethyl ether, ethylene glycol monoethyl ether, ethylene glycol monopropyl ether, ethylene glycol dimethyl ether, ethylene glycol diethyl ether, propylene glycol monomethyl ether, propylene glycol monoethyl ether, propylene glycol dimethyl ether, tetrahydrofuran, dioxane, dimethoxyethane, diglyme; ketones such as acetone, butanone, N-methylpyrrolidone, diethyl ketone; hydrocarbons such as n-pentane, n-hexane, heptane, aromatic hydrocarbons such as toluene, benzene, xylene, chlorobenzene, dichlorobenzene; halogenated alkanes such as dichloromethane, chloroform or 1,2-dichloroethane, carbon tetrachloride; acids such as acetic acid, propionic acid; nitriles such as acetonitrile, propionitrile;

The definition of the corresponding acid is the same as the definition of X in the formula (I).

The reaction temperature varies with reactants or solvents, and is usually from −20° C. to 200° C., preferably from 0° C. to 100° C.

The reaction time is not limited and is usually from 10 minutes to 10 hours.

The hydrogen chloride may be present in gaseous form, or in aqueous or non-aqueous solvent, such as hydrochloric acid, hydrogen chloride in methanol, hydrogen chloride in ethanol.

2. Methods for Preparing a Variety of Polymorphs of the Salt of Compound Z (Compound of Formula I)

In another aspect of the present invention, it provides a polymorph of the salt of compound Z (i.e. compound of formula I) and a preparation method thereof. A seed crystal may be added as needed in the process. The seed crystal herein refers to a "seed" of crystalline substance of a compound of formula (I) or homemade compound of formula (I), which is used to induce crystallization.

The polymorph of the salt of compound Z (i.e. the compound of formula I) may be prepared by one of the following methods:
Method I:
1) dissolving the basic compound Z in a third solvent to form solution C;
2) dissolving a corresponding acid X in a fourth solvent to form solution D;
3) adding solution C to solution D, or adding solution D to solution C, or directly adding a corresponding acid X to solution C to prepare a mixed solution E;
4) optionally, adding a fifth solvent to the mixed solution E;
5) precipitating the target compound by standing, or by stirring, or by adding a corresponding seed crystal to the solution prepared in step 4);
Method II:
1) dissolving a salt of compound Z (i.e., a compound of formula (I)) in a third solvent to form solution F;
2) optionally, adding a fifth solvent to solution F;
3) precipitating the target compound by standing, or by stirring, or by adding a corresponding seed crystal to the solution prepared in step 2);
Method III:
1) dissolving a salt of compound Z (i.e., a compound of formula (I)) in a third solvent to form suspension G;
2) optionally, adding a fifth solvent to solution G;
3) heating, stirring, cooling to precipitate the target compound, or adding a seed crystal to the solution prepared in step 2) to precipitate.

Preferably, the polymorph of the compound of formula (I-A) may be prepared by one of the following methods:
Method I:
1) dissolving the basic compound Z in a third solvent to form solution C;
2) dissolving hydrogen chloride in a fourth solvent to form solution D;
3) adding solution C to solution D, or adding solution D to solution C, or directly adding hydrogen chloride to solution C to prepare a mixed solution E;
4) optionally, adding a fifth solvent to the mixed solution E;
5) precipitating the target compound by standing, or by stirring, or by adding a corresponding seed crystal to the solution prepared in step 4).
Method II:
1) dissolving compound of formula (I-A) in a third solvent to form solution F;
2) optionally, adding a fifth solvent to solution F;
3) precipitating the target compound by standing, or by stirring, or by adding a corresponding seed crystal to the solution prepared in step 2);
Method III:
1) dissolving the compound of formula (I-A) in a third solvent to form suspension G;
2) optionally, adding a fifth solvent to solution G;
3) heating, stirring, and cooling to precipitate the target compound, or adding a seed crystal to the solution prepared in step 2) to precipitate.

Wherein, the third solvent, the fourth solvent and the fifth solvent may be the same or different, and the definitions of the third solvent, the fourth solvent and the fifth solvent are the same as the definition of the first solvent and the second solvent, and the temperature range is the same to that for preparing the salt of compound Z (i.e. the compound of formula I).

In particular, the preferred preparation method of the crystalline form A of the hydrochlorate of compound Z is as follows:
Adding compound Z to an alcohol, adding hydrochloric acid, heating, optionally adding activated carbon for decolorizing, adding an ester to the obtained filtrate, standing or stirring, and then separating the precipitated solid to obtain the crystal form A of compound of formula (I-A).

In particular, the crystalline form A of the hydrochlorate of compound Z is preferably prepared by the method as follows: adding hydrochlorate of compound Z to an alcohol, dissolving it by heating, cooling to precipitate a solid, then separating to give the crystalline form A of the hydrochlorate of compound Z.

In particular, the crystalline form A of the hydrochlorate of compound Z is preferably prepared by the method as follows: adding hydrochlorate of compound Z to the mixed system of an ester and an alcohol, dissolving it by heating, cooling to precipitate a solid, then separating to give the crystalline form A of the hydrochlorate of compound Z.

The alcohol is preferably a C1-C4 linear or branched alkanol, such as methanol, ethanol, isopropanol; more preferably ethanol.

The ester includes, but is not limited to, ethyl acetate, methyl acetate, propyl acetate, butyl acetate, methyl formate, ethyl formate, propyl formate, butyl formate; more preferably ethyl acetate.

3. Characterization of Salt of Compound Z (Compound of Formula I)

In general, a deviation may occur in the range of ±0.2° of the diffraction angle (2θ) in powder X-ray diffraction. Therefore, the value of the diffraction angle should be understood to include the values ±0.2°. The present invention includes not only crystals which have completely coincident peaks (diffraction angles) with those in the powder X-ray diffraction patterns, but also includes crystals which have coincident peaks (diffraction angle) with those in a deviation range of ±0.2°.

(1) Characterization of Crystalline Form A of Hydrochlorate of Compound Z

The present invention provides a crystalline form A of hydrochlorate of compound Z, which is a monohydrate.

X-ray powder diffraction data of crystalline form A of hydrochlorate of compound Z are as follows: the crystalline form has diffraction peaks at diffraction angles of 2θ 6.1°±0.2°, 9.3°±0.2°, 11.1°±0.2°, 12.2°±0.2°, 15.3°±0.2°, 16.7°±0.2°, 21.6°±0.2°, 22.9°±0.2° in X-ray powder diffraction pattern.

A single crystal X-ray diffraction analysis is carried out on the single crystals of form A, it shows from the single crystal X-ray diffraction pattern that the form A comprises one molecular of bound water. In the infrared absorption spectrum measured by the potassium bromide pellet technique, the crystalline form A has characteristic peaks at least at about 3482.81 $cm^{-1}$, 3405.67 $cm^{-1}$, 3293.82 $cm^{-1}$, 3046.98 $cm^{-1}$, 2967.91 $cm^{-1}$, 2871.49 $cm^{-1}$, 1656.55 $cm^{-1}$, 1604.48 $cm^{-1}$, 1579.41 $cm^{-1}$, 1494.56 $cm^{-1}$, 1226.50 $cm^{-1}$, 973.88 $cm^{-1}$, 813.81 $cm^{-1}$.

In the Raman spectrum, the crystal form A has characteristic peaks at least at about 3163.21 $cm^{-1}$, 2961.12 $cm^{-1}$, 2932.78 $cm^{-1}$, 1662.17 $cm^{-1}$, 1620.11 $cm^{-1}$, 1606.17 $cm^{-1}$, 1561.04 $cm^{-1}$, 1542.89 $cm^{-1}$, 1422.64 $cm^{-1}$, 1292.54 $cm^{-1}$, 1267.48 $cm^{-1}$, 1244.31 $cm^{-1}$, 1224.67 $cm^{-1}$, 854.02 $cm^{-1}$, 825.78 $cm^{-1}$.

(2) Characterization of Crystalline Form B of Hydrochlorate of Compound Z

The invention also provides a crystalline form B of hydrochlorate of compound Z.

The crystalline form B of the hydrochlorate of compound Z has an endothermic peak at 211.36° C. determined by DSC, the spectrum data are as follows:

Initial value (Onset)=211.36±3° C., peak value (Peak)=214.03±3° C.

The DSC measurement conditions are as follows:

Instrument Model: Perkin Elmer DSC 8500, temperature range: 50-280° C., scan rate: 10° C./min, nitrogen flow rate: 50 ml/min.

X-ray powder diffraction data of crystalline form B of the hydrochlorate of compound Z are as follows: the crystalline form has diffraction peaks at diffraction angle of 2θ 12.5°±0.2°, 12.8°±0.2°, 13.5°±0.2°, 14.1°±0.2°, 17.9°±0.2°, 19.5°±0.2°, 19.9°±0.2°, 23.0°±0.2°, 26.5°±0.2°, 26.8°±0.2° in X-ray powder diffraction pattern.

In the Raman spectrum, the crystal form B has characteristic peaks at least at about 3163.44 $cm^{-1}$, 2965.94 $cm^{-1}$, 2927.45 $cm^{-1}$, 2877.46 $cm^{-1}$, 1689.06 $cm^{-1}$, 1617.18 $cm^{-1}$, 1600.94 $cm^{-1}$, 1552.40 $cm^{-1}$, 1537.62 $cm^{-1}$, 1404.60 $cm^{-1}$, 1242.62 $cm^{-1}$, 657.62 $cm^{-1}$.

(3) Characterization of the Amorphous Form of Hydrochlorate of Compound Z

The present invention further provides an amorphous form of the hydrochlorate of compound Z, the X-ray powder diffraction pattern of which is substantially as shown in FIG. 7.

Accordingly, in another aspect, the present invention provides a pharmaceutical composition comprising one or more compounds of formula (I) and pharmaceutically acceptable adjuvants. The pharmaceutical composition preferably comprises one or more selected from maleate, succinate, methanesulfonate, citrate, hydrochloride, tartrate, fumarate, mucate, acetate and sulfates of compound Z. More preferably, the pharmaceutical composition comprises the crystalline form A of the hydrochlorate of compound Z having an X-ray powder diffraction pattern listed in table 1.

The adjuvant may be an excipient, binder, lubricant, disintegrator, colorant, flavoring agent, emulsifier, surfactant, solubilizer, suspending agent, isotonic agent, buffer, preservative, antioxidant, stabilizer, absorption enhancer, and the like, which are commonly used in the medical field. The above may be appropriately used in combination as needed.

Preferably, the salt of compound Z of the present invention will be formulated with at least one pharmaceutical adjuvant in the oral pharmaceutical composition, and each dosage contains 10 mg~200 mg active ingredient.

When preparing a solid composition tablet, the main active ingredient is mixed with one pharmaceutical carrier such as starch, lactose, magnesium stearate or the like, and a sugar-coating or other suitable substance may be coated on the tablet. Or the tablets are treated to prolong or delay the releasing, so that the tablets can continuously release a predetermined amount of active ingredient.

Alternatively, the active ingredient is mixed with a diluent, and the resulting mixture is filled into a capsule to obtain a capsule.

The acid addition salt of compound Z of the present invention (i.e. the compound of formula I), when used as a therapeutic or prophylactic agent for the above diseases, may be used alone or with a suitable pharmacologically acceptable adjuvant, diluent or the like, and administered in an oral manner such as a tablet, a capsule, a granule, a powder or a syrup, or in a non-oral manner such as an injection, a powder injection, a spray or a suppository.

These preparations can be prepared by a conventional method.

The amount of drug varies with symptoms, age and the like. For example, for adults, it can be administered 1 to 7 times per 1 to 7 days, and the administer amount is from 0.01 mg to 1000 mg. The administration method is not limited.

A further aspect of the present invention provides a use of the compound represented by formula (I) in preparing a medicament for preventing or treating diseases associated with PDE5 enzyme. The diseases associated with PDE5 enzyme are erectile dysfunction, pulmonary artery hypertension, female sexual dysfunction, premature labor, dysmenorrhea, benign prostatic hyperplasia, bladder outlet obstruction, incontinence, unstable and variant angina, hypertension, congestive heart failure, renal failure, atherosclerosis, stroke, peripheral vascular disease, Raynaud's disease, inflammatory disease, bronchitis, chronic asthma, allergic asthma, allergic rhinitis, glaucoma or diseases characterized by intestinal peristalsis disorders.

EFFECT OF INVENTION

Figure 1:
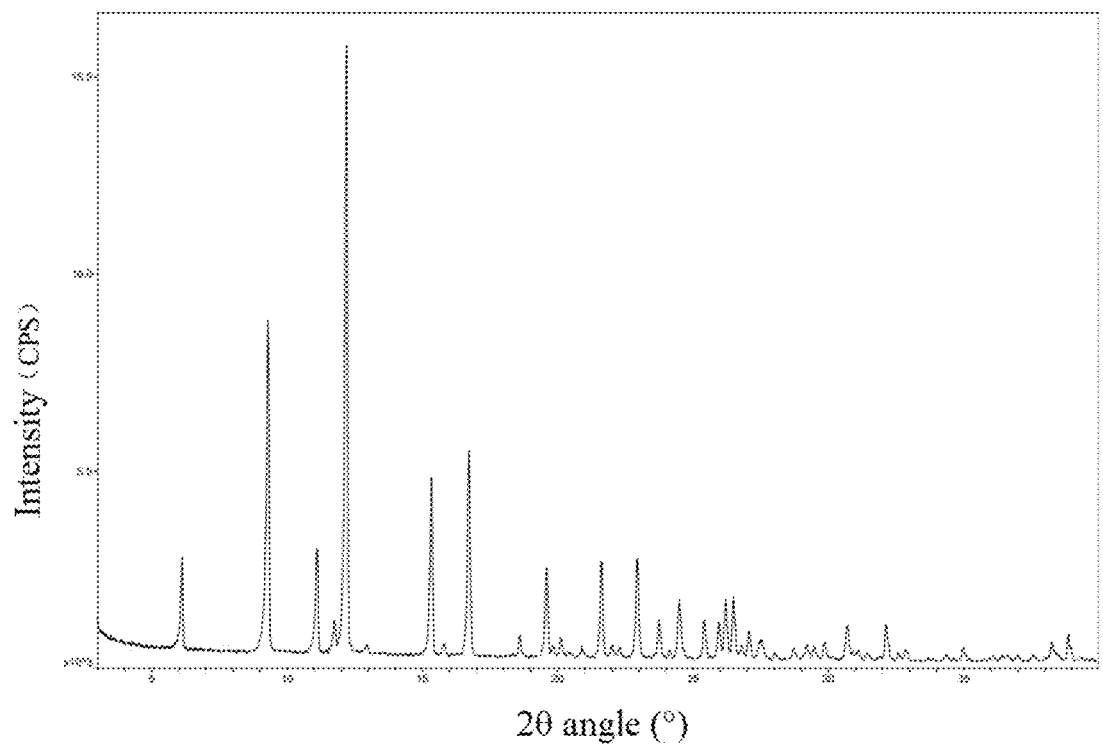
FIG. 1 is an X-ray powder diffraction pattern of crystalline form A of compound of formula (I-A)

The salt of compound Z provided by the present invention has the advantages of high stability, improved water solubility, no bad odor, and the like.

The various crystalline forms of the different salts of compound Z provided by the invention have the advantages of low hygroscopicity, good chemical stability, high purity, constant composition, simple preparation method with good reproducibility, easy storage of samples and the like.

DETAILED DESCRIPTION OF THE EMBODIMENTS

The invention is further illustrated by the following examples, which are merely used to illustrate the preferred embodiments of the invention, and are not intended to limit the invention. The temperatures and reagents applied in the following examples can be replaced with the corresponding temperatures and reagents described above to achieve the objectives of the present invention.

In the following examples, elemental analysis is carried out by using ElementarVario EL device; mass spectrometry is carried out with MAT-95 mass spectrometer (a Finnigan Corporation); NMR spectroscopy is obtained on the Mercury-300 and Mercury-400 NMR Spectrometer (Varian, Inc.); IR Absorption spectroscopy test instrument: American Nicolet Magna FTIR 6700 Fourier transform infrared spectrometer; Raman Spectrometer: Thermo Scientific DXR Raman Microscope. The infrared and Raman spectrum wave number ($cm^{-1}$) may contain −0.5 to +0.5% of the deviation, but this level of deviation is within an acceptable range in the present invention.

Example 1: Preparation of 5,6-diethyl-2-[2-n-propoxy-5-(2-(4-methylpiperazin-1-yl)acetamido)phenyl]pyrimidine-4(3H)-one Maleate Compound Z (5 g, 0.01 mol) was suspended in 50 ml of anhydrous ethanol and the suspension was heated to 65° C. to dissolve the compound, adding maleic acid (1.16 g, 0.01 mol), heating at 65° C. for 40 minutes, then activated carbon was added into the coolish system which was maintained at this temperature for 30 minutes. The activated carbon was filtered off and the resulting filtrate was stirred at room temperature for 30 minutes to precipitate a solid. The precipitated solid was filtered and dried for 4 hours to give the target compound as a white solid (4 g), purity 99% (HPLC).

Example 2: Preparation of 5,6-diethyl-2-[2-n-propoxy-5-(2-(4-methylpiperazin-1-yl)acetamido)phenyl]pyrimidin-4(3H)-one Succinate Compound Z (5 g, 0.01 mol) was suspended in 30 ml of anhydrous ethanol and the suspension was heated to 65° C. to dissolve the compound, adding succinic acid (1.18 g, 0.01 mol), stirring at 65° C. for 40 minutes, then activated carbon was added into the coolish system to decolorize. The activated carbon was filtered off and the resulting filtrate was stirred at room temperature for 30 minutes to precipitate a solid. The precipitated solid was filtered and dried to give the target compound as a white solid (3 g), purity 99% (HPLC).

Example 3: Preparation of 5,6-diethyl-2-[2-n-propoxy-5-(2-(4-methylpiperazin-1-yl)acetamido)phenyl]pyrimidin-4(3H)-one Fumarate Compound Z (5 g, 0.01 mol) was suspended in 30 ml of anhydrous ethanol and the suspension was heated to 65° C. to dissolve the compound, adding fumaric acid (1.16 g, 0.01 mol), stirring at 65° C. for 40 minutes, then activated carbon was added into the coolish system to decolorize. The activated carbon was filtered off and the resulting filtrate was stirred at room temperature for 30 minutes to precipitate a solid. The precipitated solid was filtered and dried to give the target compound as a white solid (3 g), purity 99% (HPLC).

Example 4: Preparation of 5,6-diethyl-2-[2-n-propoxy-5-(2-(4-methylpiperazin-1-yl)acetamido)phenyl]pyrimidin-4(3H)-one Acetate Compound Z (5 g, 0.01 mol) was suspended in 30 ml of anhydrous ethanol and the suspension was heated to 65° C. to dissolve the compound, adding acetic acid (0.6 g, 0.01 mol), stirring at 65° C. for 40 minutes, then activated carbon was added into the coolish system to decolorize. The activated carbon was filtered off and the resulting filtrate was stirred at room temperature for 30 minutes to precipitate a solid. The precipitated solid was filtered off and dried to give the target compound as a white solid (3 g), purity 99% (HPLC).

Example 5: Preparation of 5,6-diethyl-2-[2-n-propoxy-5-(2-(4-methylpiperazin-1-yl)acetamido)phenyl]pyrimidin-4(3H)-one Methanesulfonate Compound Z (5 g, 0.01 mol) was suspended in 40 ml of anhydrous ethanol, methanesulfonic acid 1 ml was added thereto under an ice bath, after that, temperature was raised to 60~70° C., and the mixture was stirred for 30 minutes, decolorized by activated carbon. The activated carbon was filtered off, and the filtrate was concentrated to small volume under reduced pressure, adding ethyl acetate 80 ml, stirring, then the product was gradually precipitated, suction filtered and dried to give the target compound 4.4 g.

Example 6: Preparation of 5,6-diethyl-2-[2-n-propoxy-5-(2-(4-methylpiperazin-1-yl)acetamido)phenyl]pyrimidin-4(3H)-one Tartrate Compound Z (5 g, 0.01 mol) was dissolved in 25 ml of anhydrous ethanol, tartaric acid 1.5 g was added thereto, after that, the mixture was heated to 60~70° C., stirred to react for 30 minutes, cooled to room temperature, and stirred overnight, and then the white solid was precipitated, filtered off and dried to give the target compound 4 g.

Example 7: Preparation of 5,6-diethyl-2-[2-n-propoxy-5-(2-(4-methylpiperazin-1-yl)acetamido)phenyl]pyrimidin-4(3H)-one Mucate Compound Z (5 g, 0.01 mol) was dissolved in 25 ml of anhydrous ethanol, adding mucic acid 2.1 g, after that, the mixture was heated to 60~70° C., stirred to react for 30 minutes, cooled to room temperature, and stirred overnight, and then the white solid was precipitated, filtered and dried to give the target compound 4 g.

Example 8: Preparation of 5,6-diethyl-2-[2-n-propoxy-5-(2-(4-Methylpiperazin-1-yl)acetamido)phenyl]pyrimidin-4(3H)-one Hydrochlorate Compound Z (51 g, 0.11 mol) was taken and added with acetonitrile (200 ml), concentrated hydrochloric acid 10.5 ml was added dropwise under an ice bath, after the dropping was complete, the mixture was heated under reflux for 1 hour, decolorized by activated carbon, and filtered. The filtrate was cooled to room temperature, concentrated to small volume and the product was gradually precipitated under stirring, filtered off and dried to give the target compound as a white solid 50 g. High performance liquid phase detection was carried out, purity >99%. ESI-MS: 442 (M+1). $^1$H NMR (400 MHz, DMSO-$d_6$) δ 0.96 (t, 3H), 1.03 (t, 3H), 1.19 (t, 3H), 1.72 (m, 2H), 2.45 (q, 2H), 2.56 (q, 2H), 2.65-2.75 (br, 5H), 2.90-3.03 (br, 2H), 3.03-3.17 (br, 2H), 3.25 (s, 2H), 3.30-3.40 (br, 2H), 4.01 (t, 2H), 7.13 (d, 1H), 7.79 (dd, 1H), 8.00 (d, 1H), 10.02 (s, 1H), 10.86 (br, 1H), 11.84 (s, 1H). $^{13}$C NMR (100 MHz, DMSO-$d_6$) δ167.54, 163.31, 161.53, 152.70, 152.40, 131.75, 123.75, 123.07, 121.57, 121.35, 113.21, 70.11, 60.07, 52.27, 49.11, 42.03, 26.93, 21.95, 18.01, 13.37, 13.09, 10.37.
Elemental Analysis:

|  | C (%) | H (%) | N (%) | Cl (%) |
|---|---|---|---|---|
| Measured value | 58.36 | 7.68 | 14.19 | 7.63 |
| Theoretical value | 58.11 | 7.72 | 14.12 | 7.15 |

Example 9: Preparation of 5,6-diethyl-2-[2-n-propoxy-5-(2-(4-methylpiperazin-1-yl)acetamido)phenyl]pyrimidine-4(3H)-one Hydrochlorate Compound Z (51 g, 0.11 mol) was suspended in a mixed solvent of 400 ml of anhydrous ethanol and 10 ml of water, adding 11 ml of concentrated hydrochloric acid dropwise under an ice bath, after that, the mixture was heated at 60° C. for 30 minutes, added with activated carbon and heated for 30 minutes under stirring. The activated carbon was filtered off, the solvent was partly removed by concentration under reduced pressure, adding 600 ml of ethyl acetate, the product was gradually precipitated, suction filtration was performed and the filtered substance was dried to give the target compound 35 g.

Example 10: Preparation of 5,6-diethyl-2-[2-n-propoxy-5-(2-(4-methylpiperazin-1-yl)acetamido)phenyl]pyrimidin-4(3H)-one Sulfate Compound Z (5 g) was suspended in a mixed solvent of 19 ml of anhydrous ethanol and 0.5 ml of water, adding 0.7 ml of concentrated sulfuric acid under an ice bath, and the mixture was heated under reflux for 30 minutes, naturally cooled to room temperature and concentrated to small volume under reduced pressure, then adding 30 ml of ethyl acetate. The product was gradually precipitated, suction filtration was performed and the filtered substance was dried to give a product 3.5 g.

Example 11: Preparation of 5,6-diethyl-2-[2-n-propoxy-5-(2-(4-methylpiperazin-1-yl)acetamido)phenyl]pyrimidin-4(3H)-one hydrochloride monohydrate (Form A)

Compound Z (51 g, 0.11 mol) was added into 400 ml of anhydrous ethanol, adding 11 ml of concentrated hydrochloric acid dropwise, after that, the mixture was heated at 60° C. for 30 minutes, the activated carbon was added thereto and the system was heated for 30 minutes under stirring. The activated carbon was filtered off, 600 ml of ethyl acetate was added into the filtrate under stirring, and the product was gradually precipitated, then suction filtration was performed and the filtered substance was dried to give the target compound 30 g.

Figure 2:
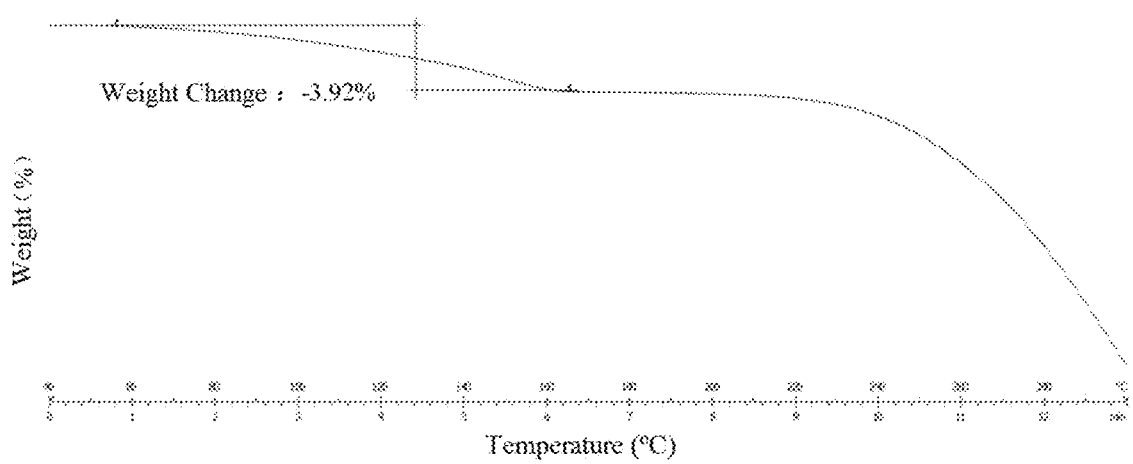
FIG. 2 is a thermogravimetric analysis diagram of crystalline form A of compound of formula (I-A)
Figure 3:
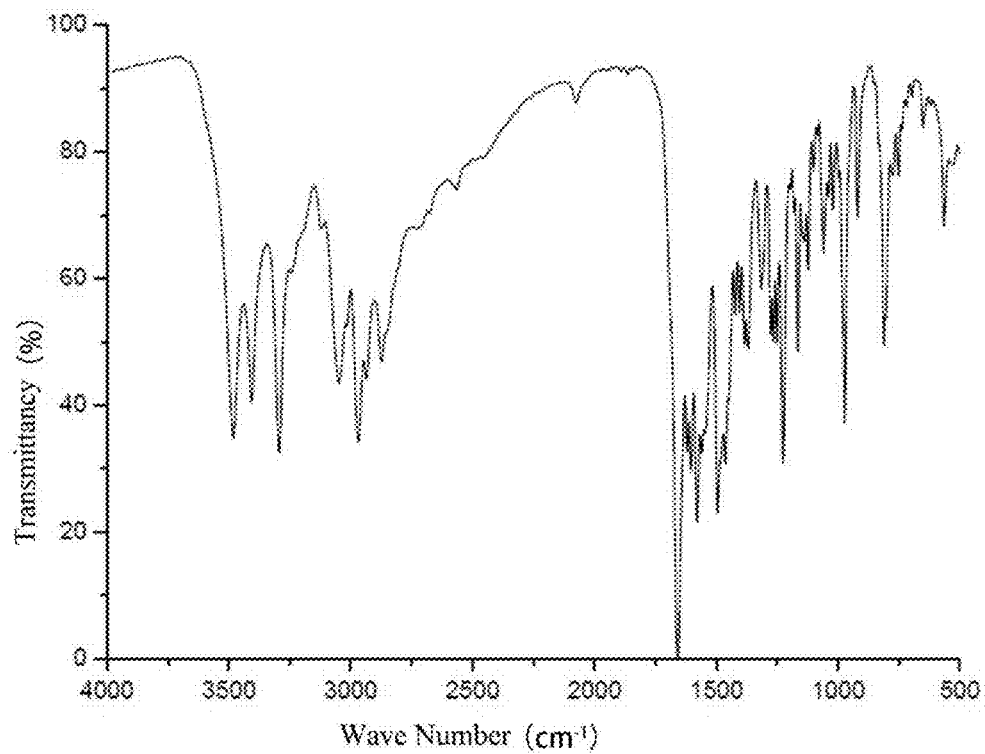
FIG. 3 is an infrared spectrum of crystalline form A of compound of formula (I-A)

It can be seen from the TGA curve that the form A had weight loss of 3.92% at 60° C.~170° C., TG spectrum was shown in FIG. 2. The test conditions are as follows: TG analytical instrument: mettler toledo TGA2 thermogravimetric analyzer; test conditions: purge gas, nitrogen 50 ml/min; heating rate: 20 K/min; temperature range: 40° C.-300° C.

Example 12: Preparation of 5,6-diethyl-2-[2-n-propoxy-5-(2-(4-methylpiperazin-1-yl)acetamido)phenyl]pyrimidin-4(3H)-one Hydrochloride Monohydrate (Form A)

The target compound (1 g) of Example 8 or 9 was added to ethanol (8 ml), dissolved under heating, and then the mixture was naturally cooled to room temperature and a white solid was gradually precipitated, filtered and dried to obtain the target compound 0.6 g as a white solid.

Example 13: Preparation of 5,6-diethyl-2-[2-n-propoxy-5-(2-(4-methylpiperazin-1-yl)acetamido)phenyl]pyrimidin-4(3H)-one Hydrochloride Monohydrate (Form A)

The target compound (1 g) of Example 8 or 9 was added to ethanol (4 ml) and ethyl acetate (5 ml), and then the mixture was naturally cooled to room temperature and a white solid was gradually precipitated, filtered and dried to obtain the target compound 0.85 g as a white solid.

Example 14: Preparation of 5,6-diethyl-2-[2-n-propoxy-5-(2-(4-methylpiperazin-1-yl)acetamido)phenyl]pyrimidin-4(3H)-one Hydrochlorate (Form B)

The target compound of Example 8 or 9 (1 g) was added into ethanol (15 ml), dissolved under heating, then adding isopropanol (15 ml), the mixture was naturally cooled to room temperature, and a white solid was gradually precipitated, filtered and dried to obtain the target compound 0.7 g as a granular crystal.

Example 15: Preparation of 5,6-diethyl-2-[2-n-propoxy-5-(2-(4-methylpiperazin-1-yl)acetamido)phenyl]pyrimidin-4(3H)-one Hydrochloride (Amorphous)

The target compound of Example 8 or 9 (200 mg) was added in chloroform (10 ml), stirring at room temperature, volatizing slowly, and a white solid was precipitated, filtered and dried to obtain the target compound 0.15 g as a sheet-like solid.

Example 16: Preparation of 5,6-diethyl-2-[2-n-propoxy-5-(2-(4-methylpiperazin-1-yl)acetamido)phenyl]pyrimidin-4(3H)-one (Compound Z)

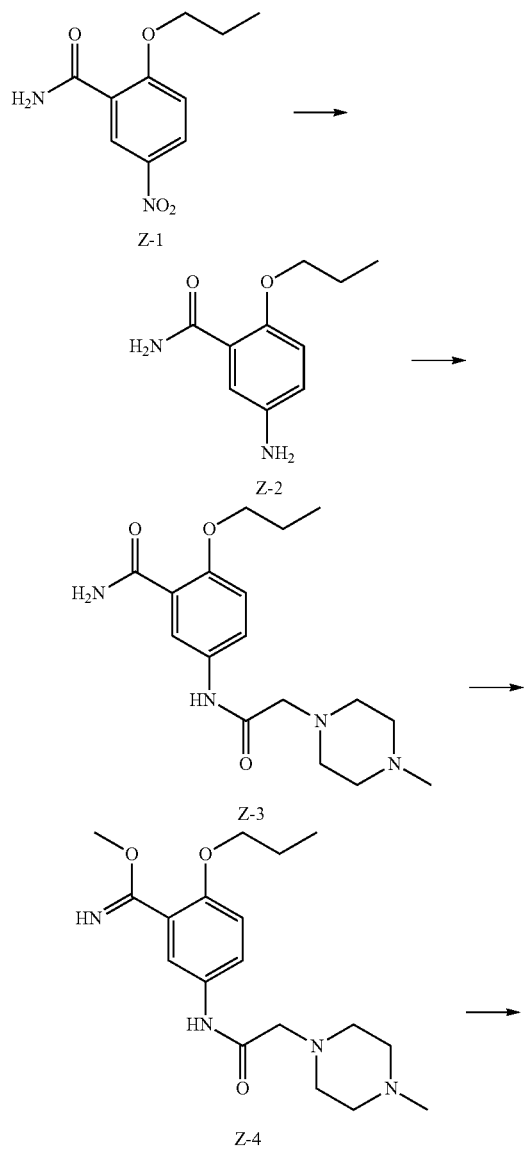

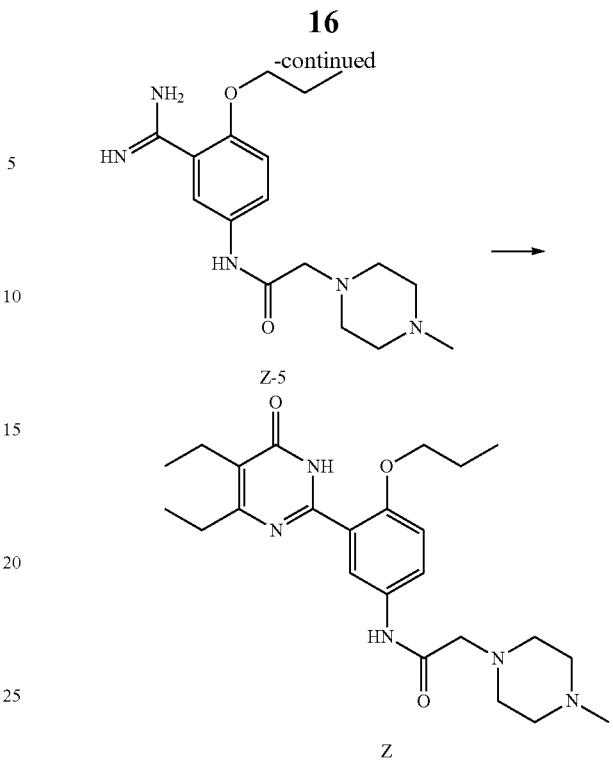

Methanol (60 ml) and compound Z-1 (log) were added into a 100 ml single-necked flask, the air therein was replaced with nitrogen for 5 times, 0.3 g of active nickel was added thereto, the nitrogen was replaced with hydrogen for 5 times, the mixture was stirred at room temperature for 12 hours, and the active nickel was removed by filtration after the reaction was complete. The filtrate was concentrated under reduced pressure to give compound Z-2 (8 g), yield 92%.

Compound Z-2 (1.94 g, 10 mmol) was added into 20 ml of dichloromethane, adding 4-methyl-1-piperazine acetic acid (1.58 g, 10 mmol) and N,N'-carbonyldiimidazole (1.94 g, 12 mmol), and the mixture was stirred at room temperature for 8 hours. After the reaction was completed, 10 ml of water was added to the reaction system, stirring, standing to let it separate, then the organic phase was concentrated to dryness to give compound Z-3 (2.34 g), yield 70%.

Compound Z-3 (334 g, 1 mol) was added to N,N-dimethylformamide (1 L), potassium carbonate (276 g, 2 mol) and dimethyl sulfate (126 g, 1 mol) were added thereto under stirring, and the mixture was heated to 40-50° C., stirred for 12 hours, and then concentrated under reduced pressure to obtain the residue. 1 L of water was added thereto, the mixture was stirred at room temperature and filtered to obtain 260 g of compound Z-4 as an off-white solid, yield 75%. ESI-MS: 349 (M+1).

Compound Z-4 (348 g, 1 mol) was dissolved in methanol (1 L), and the mixture was stirred and heated to 50° C., then ammonia gas was introduced therein slowly. Then the system was concentrated under reduced pressure to obtain the residue after the reaction was completed. 198 g of compound Z-5 was obtained by crystallization purification with methyl-tert-butyl ether, yield: 59%. ESI-MS: 334 (M+1).

Compound Z-5 (333 g, 1 mol) was dissolved in methanol (2 L), sodium methoxide (54 g, 1 mol) and methyl 2-ethyl-3-oxopentanoate (158 g, 1 mol) were added thereto, and the mixture was heated under reflux and maintained under reflux for 12 h, then cooled to room temperature. The system was adjusted by adding dilute hydrochloric acid to pH=7, and concentrated under reduced pressure to remove methanol. Ethyl acetate was added for extracting, and the solution was allowed to stand for separation, then the organic phase was concentrated to dryness to give 410 g of compound Z, yield 93%. ESI-MS: 442 (M+1). $^1$H NMR (400 MHz, CDCl$_3$) δ 1.12 (t, 6H), 1.30 (t, 3H), 1.96 (m, 2H), 2.56 (q, 2H), 2.67 (q, 2H), 2.31 (br, 3H), 2.45-2.55 (br, 4H), 2.60-2.70 (br, 4H), 3.14 (s, 2H), 4.13 (t, 2H), 6.99 (d, 1H), 7.97 (dd, 1H), 8.26 (d, 1H), 9.11 (s, 1H), 11.14 (br, 1H). $^{13}$C NMR (100 MHz, CDCl$_3$) δ167.99, 163.87, 161.74, 153.41, 150.78, 131.23, 124.33, 123.93, 121.31, 119.23, 113.06, 70.95, 61.37, 54.76, 53.05, 45.57, 27.17, 21.97, 18.24, 12.93, 12.65, 10.16.
Elemental Analysis:

|  | C (%) | H (%) | N (%) |
|---|---|---|---|
| Measured value | 65.68 | 7.80 | 15.89 |
| Theoretical value | 65.28 | 7.99 | 15.86 |

EXPERIMENTAL EXAMPLES

1. Advantages of the Salt of Compound Z (i.e. the Compound of Formula I)

(1) Comparison of Solubility of the Compounds

The solubility of compound Z prepared in Example 16 and different salts of compound Z prepared in Examples 1-7 and 9-10 was compared. An appropriate amount of the sample was weighed in a glass test tube and a selected solvent was gradually added therein to observe the clarification. The solubility of different salts in a variety of pH of 2, 4.5, 6.8 and deionized water was measured, as follows:

TABLE 1

Solubility at different pH values (mg/mL)

|  | water | pH = 2 | pH = 4.5 | pH = 6.8 |
|---|---|---|---|---|
| compound Z | 1.5 | 5.3 | 38.1 | 1.7 |
| hydrochlorate of compound Z | >25.0 | >22.8 | >23.6 | >26.6 |
| fumarate of compound Z | >26.6 | >24.2 | >20.2 | >27.0 |
| succinate of compound Z | >24.8 | >20.8 | >22.0 | >20.8 |

TABLE 1-continued

Solubility at different pH values (mg/mL)

|  | water | pH = 2 | pH = 4.5 | pH = 6.8 |
|---|---|---|---|---|
| methanesulfonate of compound Z | >23.8 | >22.4 | >25.4 | >23.2 |
| sulfate of compound Z | >20.6 | >20.2 | >25.6 | >24.4 |
| tartrate of compound Z | >153.2 | >218.7 | >155.4 | >130.5 |
| mucate of compound Z | 10.6 | 36.3 | 62.7 | 39.0 |
| acetate of compound Z | 14.0 | 35.8 | >101.8 | 22.6 |
| maleate of compound Z | 5.8 | 6.1 | 21.4 | 46.4 |

It can be seen from the above table that the solubility of the basic compound Z in water is significantly lower than that of the salts of compound Z. The solubility is an important factor for preparing the pharmaceutical formulation, oral bioavailability and the like. Therefore, the salt formation of compound Z is more advantageous for the preparation of a pharmaceutical preparation for human pharmaceutical use.

(2) Comparison of Compound Appearance and Characters

The appearance and characters of the basic compound Z prepared in Example 16 and different salts of compound Z prepared in Examples 1-2, 5-6, 9 were observed, the results are shown in the table below:

TABLE 2

Comparison of appearance and characters of various salts of compound Z

|  | Characters | odor |
|---|---|---|
| compound Z | White solid | Pungent odor |
| maleate of compound Z | White solid | No bad smell |
| hydrochlorate of compound Z | White solid | No bad smell |
| succinate of compound Z | White solid | No bad smell |
| methanesulfonate of compound Z | White solid | No bad smell |
| tartrate of compound Z | White solid | No bad smell |

As can be seen from the above table, the salts of the basic compound of compound Z can mask the original pungent odor, and are more suitable for oral administration.

(3) Comparison of Stability of the Compounds

The chemical stability of the basic compound Z prepared in Example 16 and the salts of compound Z prepared in Examples 5, 9 and 10 was compared through a stress testing, the results were shown in the table below:

TABLE 3

Stability test results of compound Z and its salts:

|  |  | compound Z | | hydrochlorate of compound Z | | methanesulfonate of compound Z | | sulfate of compound Z | |
|---|---|---|---|---|---|---|---|---|---|
|  |  | characters | purity | characters | purity | characters | purity | characters | purity |
|  | 0 days | White powder solid | 99.6% | White powder solid | 99.77% | White powder solid | 99.66% | Yellow powder solid | 99.63% |
| high temperature (60° C.) | 5 days | White powder solid | 99.69% | White powder solid | 99.65% | White powder solid | 99.54% | Yellow powder solid | 99.59% |
|  | 10 days | White powder solid | 99.36% | White powder solid | 99.71% | White powder solid | 99.49% | Yellow powder solid | 99.64% |

TABLE 3-continued

Stability test results of compound Z and its salts:

|  |  | compound Z |  | hydrochlorate of compound Z |  | methanesulfonate of compound Z |  | sulfate of compound Z |  |
|---|---|---|---|---|---|---|---|---|---|
|  |  | characters | purity | characters | purity | characters | purity | characters | purity |
| High humidity (25° C., 92.5% RH) | 5 days | White powder solid | 99.64% | White powder solid | 99.73% | Yellow liquid | 99.54% | Yellow powder solid attached to the weighing bottle | 99.64% |
|  | 10 days | White powder solid | 99.53% | White powder solid | 99.77% | Yellow liquid | 99.55% | Yellow powder solid, attached to the weighing bottle, completely absorbing moisture | 99.62% |
| illumination (4500 lx ± 500 lx) | 5 days | Yellowish surface | 99.37% | White powder solid | 99.79% | White powder solid | 99.72% | Yellow powder solid | 97.43% |
|  | 10 days | Yellowish surface | 97.99% | White powder solid | 99.72% | White powder solid | 99.46% | Gray-yellow powder solid | 96.99% |

It can be seen from the comparison test results of the influencing factors in the above table that the salts of compound Z, especially the hydrochlorate, were stable under high temperature, light and high humidity conditions, while the stability of compound Z is relatively poor, especially under the condition of 10 days of illumination and the purity was significantly reduced.

(4) Comparison of Pharmacokinetic Properties

Figure 8:
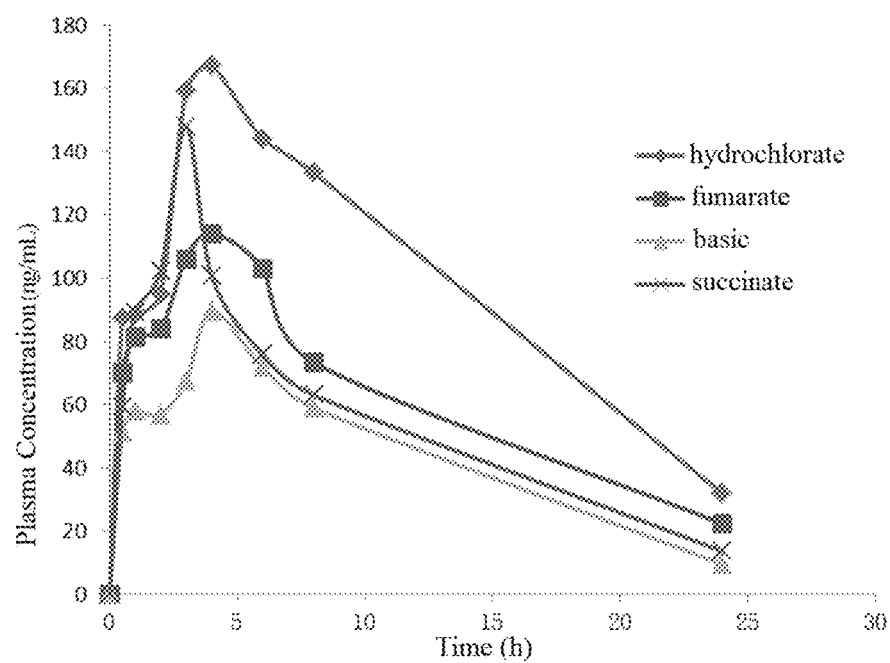
FIG. 8 is a graph showing the plasma concentration-time curve of compound Z and its different salts after administration.
Figure 9:
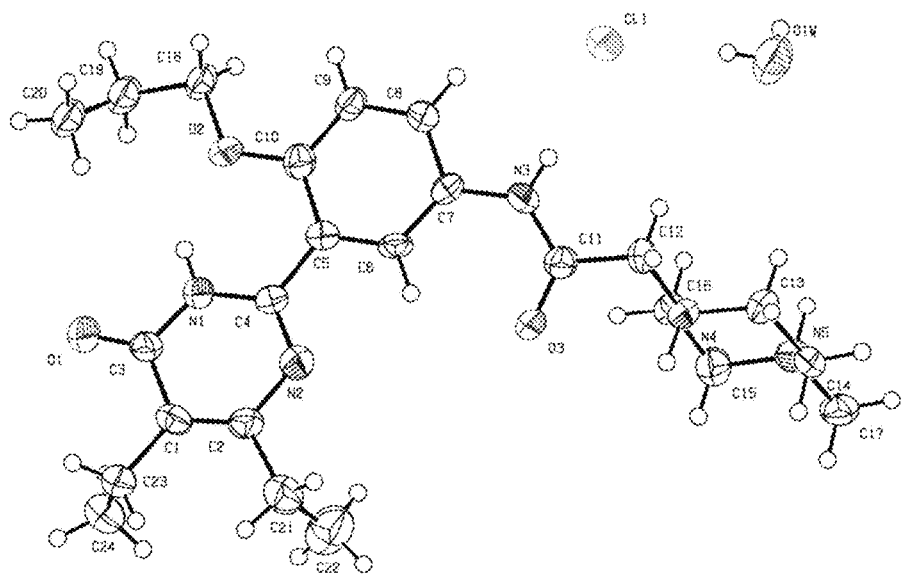
FIG. 9 is a single crystal X-ray diffraction structure of crystalline form A of compound of formula (I-A)
Figure 10:
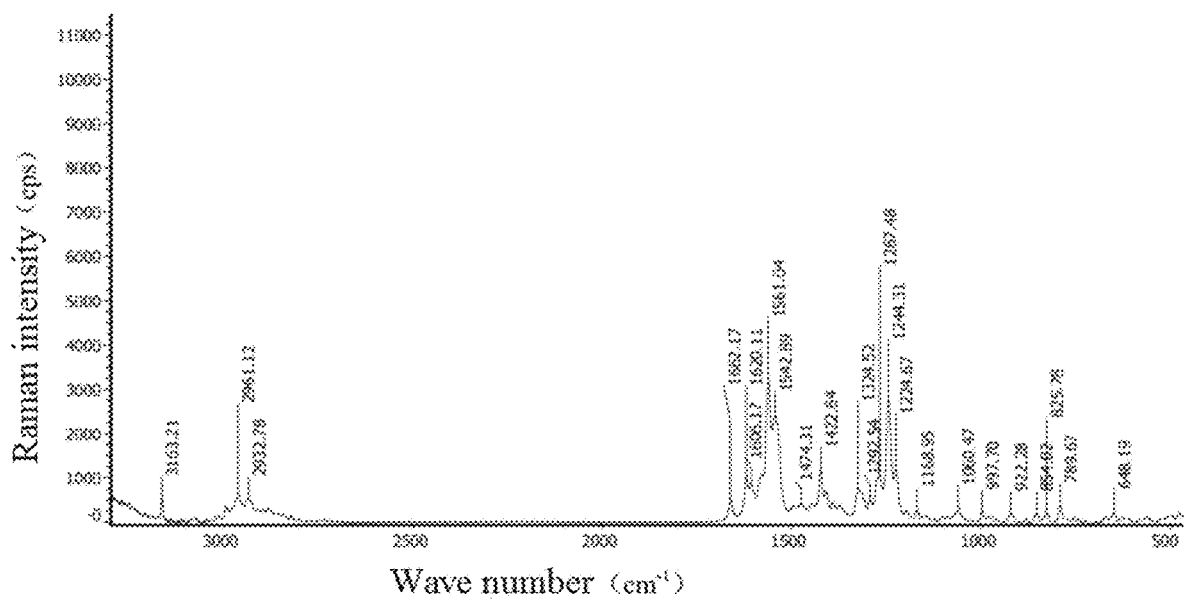
FIG. 10 is a Raman spectrum of crystalline form A of compound of formula (I-A)
Figure 11:
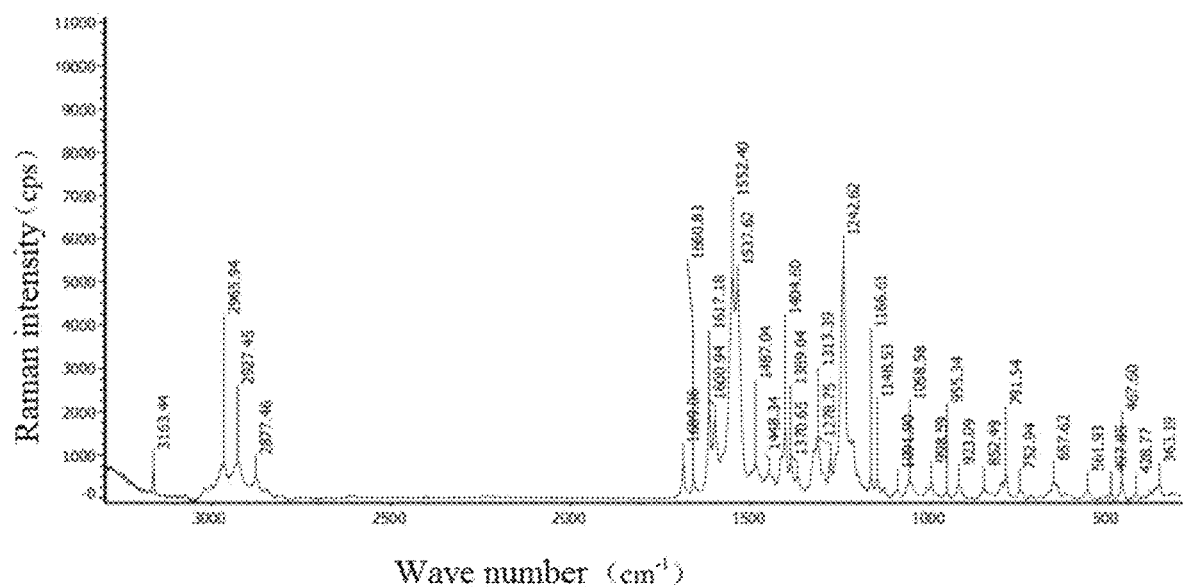
FIG. 11 is a Raman spectrum of crystalline form B of compound of formula (I-A).

The in vivo pharmacokinetic experiment in rats were carried out for the basic compound Z prepared in Example 16, the hydrochlorate of compound Z prepared in Example 9, the succinate of compound Z prepared in Example 2, the fumarate of compound Z prepared in Example 3 (administered by gavage, dose 3 mg/kg), the results were shown in FIG. 8 of the specification.

From the experimental results, it can be seen that, when compound Z is converted to a salt, the in vivo pharmacokinetic properties in rats are more advantageous than that of the basic compound Z, in particular, the hydrochlorate of compound Z has significantly better in vivo pharmacokinetic properties than compound Z.

As it can be seen from the above experimental results, the compounds represented by formula I prepared by salification of compound Z can improve the solubility of compound Z, mask the bad odor of compound Z, and increase stability. In particular, the hydrochlorate of compound Z had good physical and chemical properties (good solubility and high stability), high oral bioavailability, and the best comprehensive druggability, and is more suitable for pharmaceutical preparation applications, and more suitable for preservation.

Figure 4:
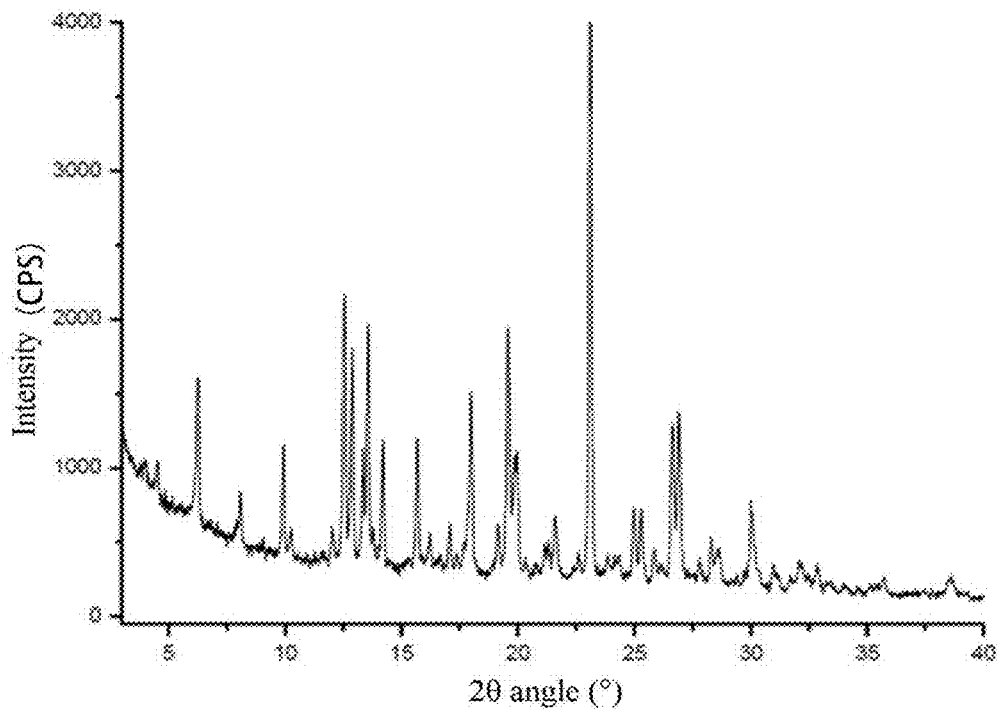
FIG. 4 is an X-ray powder diffraction pattern of crystalline form B of compound of formula (I-A)
Figure 5:
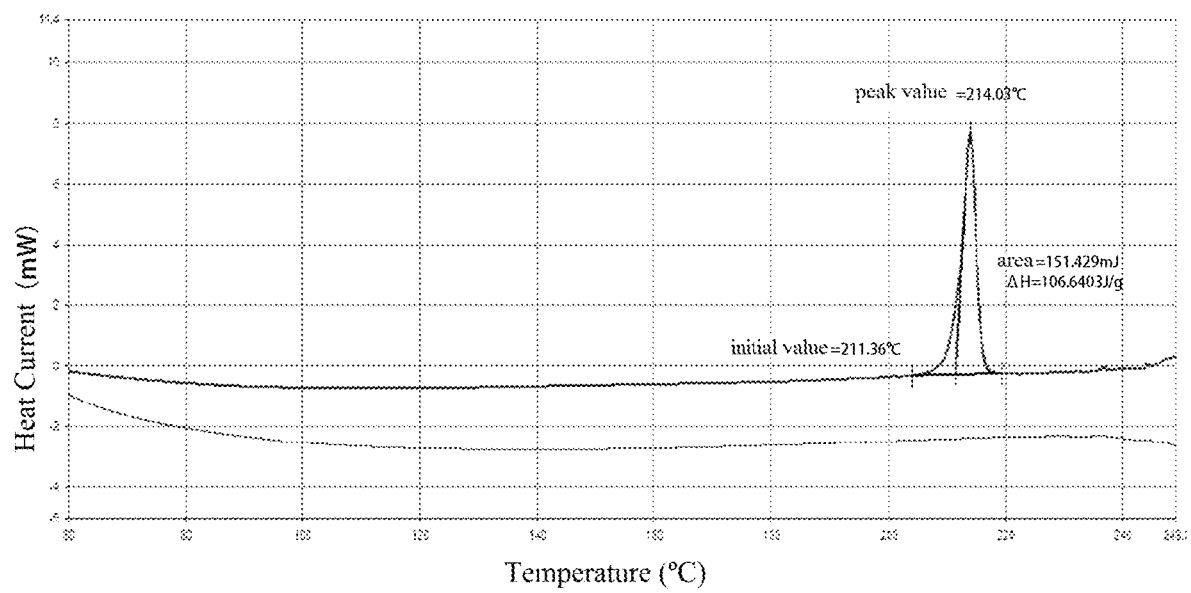
FIG. 5 is a differential scanning calorimetry diagram of crystalline form B of compound of formula (I-A)
Figure 6:
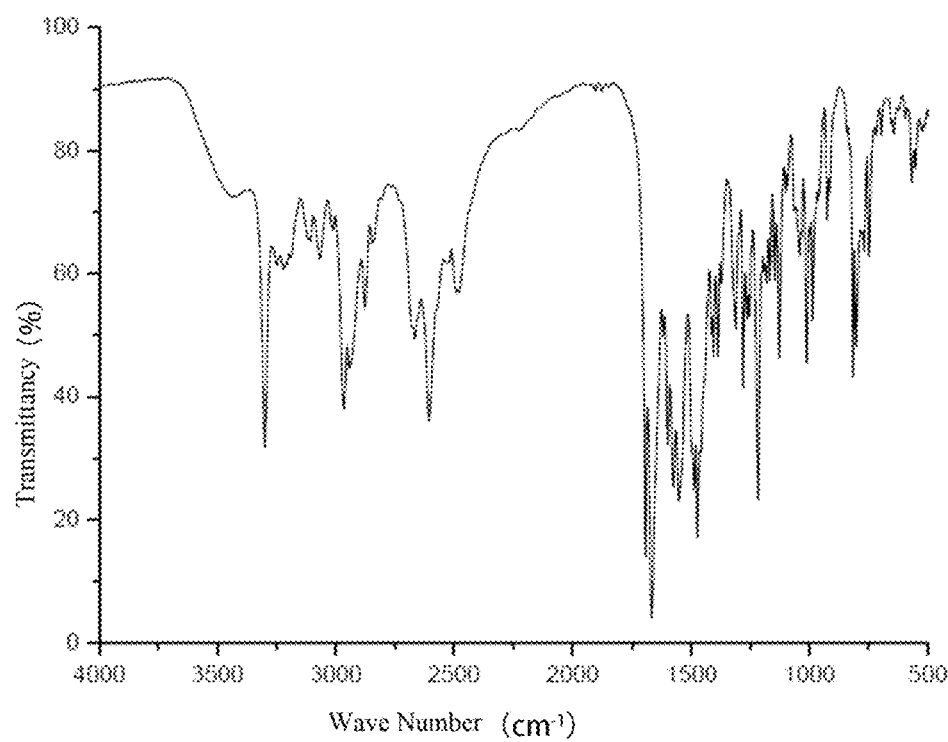
FIG. 6 is an infrared spectrum of crystalline form B of compound of formula (I-A)
Figure 7:
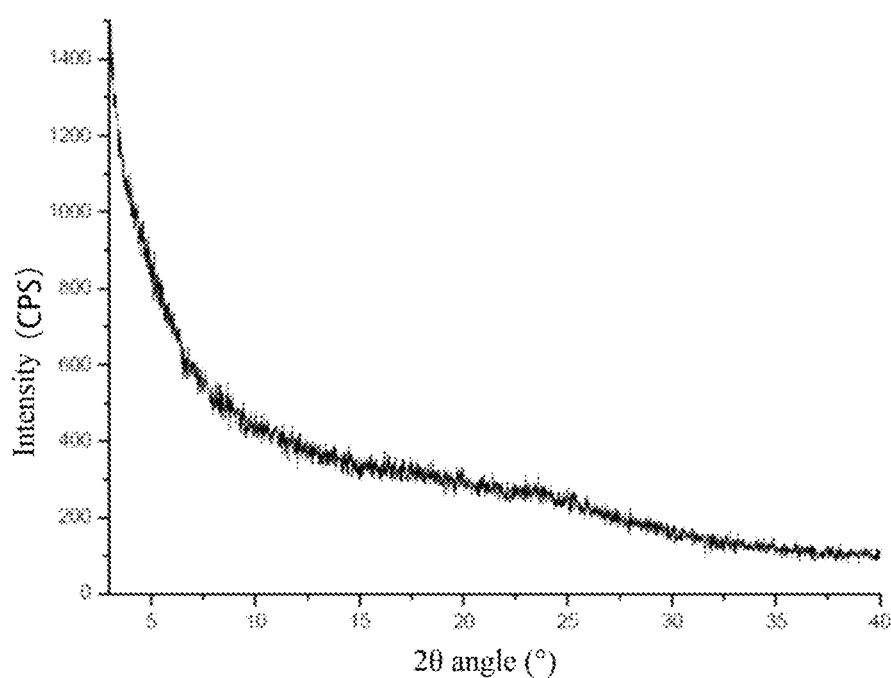
FIG. 7 is an X-ray powder diffraction pattern of the amorphous form of the compound of formula (I-A)

2. X-Ray Powder Diffraction Patterns of Crystalline Forms A and B of the Hydrochlorate of Compound Z The X-ray powder diffraction patterns of crystalline form A prepared in Examples 11 or 12, crystalline form B prepared in Example 14 and amorphous prepared in Example 15 were measured, the data were shown in Tables 4 and 5 and FIGS. 1, 4 and 7.

The X-ray powder diffraction pattern was determined under the conditions as follows:
Instrument model: Bruker D8 advance, target: Cu K α (40 kV, 40 mA), distance from sample to detector: 30 cm, scanning range: 3°-40° (2θ value), scanning step: 0.1 s.

TABLE 4

X-ray powder diffraction data for crystalline form A of hydrochlorate of compound Z

| Diffraction angle (2θ, °) | Intensity ($I/I_0$, %) |
|---|---|
| 6.122 | 15.3 |
| 9.295 | 54.8 |
| 11.103 | 17.2 |
| 11.743 | 4.0 |
| 12.198 | 100.0 |
| 15.331 | 29.5 |
| 16.717 | 33.9 |
| 19.584 | 14.4 |
| 20.127 | 3.0 |
| 21.610 | 15.7 |
| 22.934 | 16.4 |
| 23.739 | 6.1 |
| 24.496 | 9.5 |
| 25.418 | 6.3 |
| 25.957 | 5.1 |
| 26.217 | 9.1 |
| 26.499 | 8.7 |
| 32.136 | 5.9 |

TABLE 5

X-ray powder diffraction data for crystalline form B of hydrochlorate of compound Z

| Diffraction angle (2θ, °) | Intensity ($I/I_0$, %) |
|---|---|
| 8.079 | 11.3 |
| 9.918 | 19.3 |
| 10.239 | 6.5 |
| 12.521 | 46.4 |
| 12.844 | 30.2 |
| 13.321 | 17.9 |
| 13.54 | 43.6 |
| 14.177 | 14.2 |
| 15.642 | 20.8 |
| 17.339 | 3.9 |
| 17.942 | 35.8 |
| 19.523 | 54.7 |
| 19.919 | 48.7 |
| 23.058 | 100 |
| 24.905 | 14.7 |
| 26.562 | 49 |
| 26.859 | 34.9 |
| 28.24 | 10.8 |
| 29.942 | 25.6 |
| 32.121 | 16 |

TABLE 5-continued

X-ray powder diffraction data for crystalline form B of hydrochlorate of compound Z

| Diffraction angle (2θ, °) | Intensity ($I/I_0$, %) |
|---|---|
| 35.638 | 7.4 |
| 38.518 | 9.7 |
| 39.161 | 24.2 |
| 39.74 | 8.9 |

3. The Superiority of Crystalline Form a of Hydrochlorate of Compound Z

The properties of crystalline form A prepared in Examples 11 or 12, crystalline form B prepared in Example 14 and amorphous substance prepared in Example 15 were compared, the results were shown in the following table 6.

TABLE 6

Comparison of properties of various solid forms of hydrochlorate of compound Z

| Crystal form | hygroscopicity | Crystal stability |
|---|---|---|
| form A | 65% RH, water absorption 2.48% | stable |
|  | 80% RH, water absorption 3.41% |  |
| form B | 65% RH, water absorption 3.58% | transformed to form A |
|  | 80% RH, water absorption 11.3% |  |
| Amorphous | 65% RH, water absorption 16.53% | transformed to form A |
|  | 80% RH, water absorption 6.74% |  |

As can be seen from the above table, the crystal form A has stable properties and low hygroscopicity, and is a preferred crystal form.

The invention claimed is:

1. A compound of the following formula:

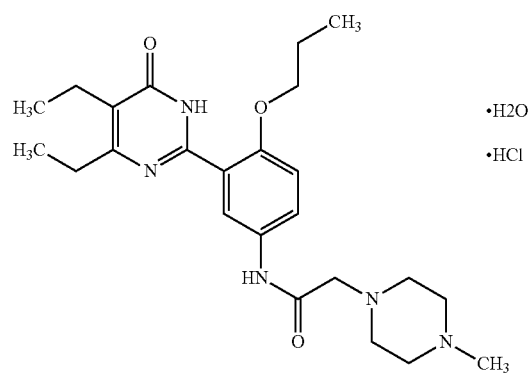

wherein the compound is a crystalline form A which has peaks at a diffraction angle 2θ of 6.1°±0.2°, 9.3°±0.2°, 11.1°±0.2°, 12.2°±0.2°, 15.3°±0.2°, 16.7°±0.2°, 21.6°±0.2°, 22.9°±0.2° in X-ray diffraction pattern.

2. The compound according to claim 1, wherein the crystalline form A has characteristic peaks at least at 3482.81 $cm^{-1}$, 3405.67 $cm^{-1}$, 3293.82 $cm^{-1}$, 3046.98 $cm^{-1}$, 2967.91 $cm^{-1}$, 2871.49 $cm^{-1}$, 1656.55 $cm^{-1}$, 1604.48 $cm^{-1}$, 1579.41 $cm^{-1}$, 1494.56 $cm^{-1}$, 1226.50 $cm^{-1}$, 973.88 $cm^{-1}$, 813.81 $cm^{-1}$, in the infrared absorption spectrum as measured by the potassium bromide pellet technique.

3. The compound according to claim 1, wherein the crystalline form A belongs to monoclinic crystal system and space group Pc, with axis length a=9.935(4) Å, b=14.44(6) Å, c=9.147(5) Å, and the angle of the lattice plane α=90°, β=106.47(5°), γ=90°.

4. A pharmaceutical composition comprising the compound according to claim 1 and a pharmaceutically acceptable adjuvant.

* * * * *